(12) United States Patent  
Shimizu (10) Patent No.: US 9,395,303 B2  
(45) Date of Patent: Jul. 19, 2016

(54) FLUORESCENCE DETECTION DEVICE AND FLUORESCENCE DETECTION METHOD

(71) Applicant: Mitsubishi Rayon Co., Ltd., Chiyoda-ku (JP)

(72) Inventor: Kouji Shimizu, Yokohama (JP)

(73) Assignee: Mitsubishi Rayon Co., Ltd., Chiyoda-ku (JP)

(*) Notice: Subject to any disclaimer, the term of this patent is extended or adjusted under 35 U.S.C. 154(b) by 0 days.

(21) Appl. No.: 14/371,571

(22) PCT Filed: Mar. 12, 2013

(86) PCT No.: PCT/JP2013/056795  
§ 371 (c)(1),  
(2) Date: Jul. 10, 2014

(87) PCT Pub. No.: WO2013/137247  
PCT Pub. Date: Sep. 19, 2013

(65) Prior Publication Data  
US 2015/0008337 A1    Jan. 8, 2015

(30) Foreign Application Priority Data

Mar. 12, 2012   (JP) .................................. 2012-054942

(51) Int. Cl.  
*G01N 21/64* (2006.01)  
*G01N 21/59* (2006.01)

(52) U.S. Cl.  
CPC ............ *G01N 21/6486* (2013.01); *G01N 21/59* (2013.01); *G01N 21/6452* (2013.01);

(Continued)

(58) Field of Classification Search  
CPC .......... G01N 21/6452; G01N 21/6428; G01N 21/17; G01N 21/6486; G01N 21/59; G01N 2201/062; G01N 2201/06113; G01N 2201/08; G01N 2201/6491  
USPC ........................................... 250/458.1, 459.1  
See application file for complete search history.

(56) References Cited

U.S. PATENT DOCUMENTS

2004/0234114 A1* 11/2004 Amakawa .......... G01N 21/6452  
382/128  
2006/0194308 A1*  8/2006 Gutekunst ................. G01J 3/02  
435/288.7

(Continued)

FOREIGN PATENT DOCUMENTS

JP        2005 30919          2/2005  
JP        2005 062023         3/2005

(Continued)

OTHER PUBLICATIONS

International Search Report Issued Jun. 18, 2013 in PCT/JP13/056795 Filed Mar. 12, 2013.

*Primary Examiner* — Yara B Green  
(74) *Attorney, Agent, or Firm* — Oblon, McClelland, Maier & Neustadt, L.L.P.

(57) ABSTRACT

Provided is a fluorescence detection device that is capable of accurately detecting the intensity of fluorescence from a sample, even when using a microarray in which a sample having a certain degree of thickness in a direction of irradiating the sample with excitation light is disposed. The fluorescence detection device (6) according to the invention detects fluorescence from a translucent sample (4) containing a fluorescent substance. The fluorescence detection device includes an excitation light irradiation unit (12) that irradiates the sample with excitation light, a detection unit (18) that detects fluorescence from the sample, and an irradiation angle adjustment unit (14) that adjusts an irradiation angle of the excitation light with respect to the sample in accordance with dimensions of the sample.

13 Claims, 4 Drawing Sheets

(52) U.S. Cl.
CPC .. *G01N2021/6491* (2013.01); *G01N 2201/062* (2013.01); *G01N 2201/06113* (2013.01); *G01N 2201/08* (2013.01)

(56) References Cited

U.S. PATENT DOCUMENTS

| | | | |
|---|---|---|---|
| 2007/0269085 A1 | 11/2007 | Oshiro et al. | |
| 2008/0225278 A1 | 9/2008 | Namba et al. | |
| 2009/0152474 A1* | 6/2009 | Berger | G01N 21/6456 250/484.4 |
| 2009/0189087 A1* | 7/2009 | Suzuki | G01N 21/6452 250/458.1 |
| 2010/0019157 A1 | 1/2010 | Furlan et al. | |
| 2010/0140503 A1* | 6/2010 | Sugiura | G01N 21/6452 250/459.1 |
| 2010/0252751 A1* | 10/2010 | Klunder | B82Y 15/00 250/459.1 |

FOREIGN PATENT DOCUMENTS

| | | |
|---|---|---|
| JP | 2006 215025 | 8/2006 |
| JP | 2007 310231 | 11/2007 |
| JP | 2010 32513 | 2/2010 |
| JP | 4605713 B2 | 1/2011 |
| WO | 2004 063731 | 7/2004 |
| WO | 2007 037439 | 4/2007 |

\* cited by examiner

FLUORESCENCE DETECTION DEVICE AND FLUORESCENCE DETECTION METHOD

TECHNICAL FIELD

The present invention relates to a fluorescence detection device and a fluorescence detection method using the same.

BACKGROUND ART

A microarray collectively represents a material or technology in which a plurality of objects of inspection and experiment are fixed, and inspection and experiment are performed at a time. Particularly, development focused on a DNA microarray using a nucleic acid has processed in fields of biology, medicine, and pharmacy from the end of $20^{th}$ century, and the DNA microarray has been used.

For example, when using DNA microarray, mRNA is extracted from a sample, cDNA that is synthesized by inverse transcription is biotin labeled, and hybridization with DNA on a substrate of the DNA microarray is performed. In addition, a sample formed by the hybridization is irradiated with excitation light, the intensity of fluorescence that is emitted from a fluorescent substance contained in the sample is detected by a fluorescence microscope, a fluorescence laser scanner, and the like. An expression level of mRNA can be determined on the basis of the intensity of fluorescence that is detected.

A fluorescence detection device, which irradiates a sample disposed in a microarray with excitation light and detects fluorescence from the sample, is typically classified into two types including a coaxial vertical type and a non-coaxial vertical type. In the coaxial vertical type, excitation light is allowed to pass through a condensing lens provided on an optical path of the excitation light and a sample is irradiated with the excitation light. In addition, fluorescence from the sample excited by the excitation light is condensed by the same condensing lens and is focused on an imaging device.

In the coaxial vertical type, a device background rises due to intrinsic fluorescence of the condensing lens, which is generated when the excitation light passes through the condensing lens, and thus it is difficult to accurately detect weak fluorescence from the sample.

Therefore, as a device that improves the detect of the coaxial vertical type, a non-coaxial vertical type as disclosed in Patent Document 1 is known. In the device disclosed in Patent Document 1, a sample is irradiated with excitation light from an oblique lower side, and fluorescence from the sample is condensed by a lens disposed on a lower side of the sample in order for the lens not to overlap with the optical axis of the excitation light. In this device, the excitation light does not pass through the lens, and thus the intrinsic fluorescence of the lens is prevented from being generated.

CITATION LIST

Patent Document

Patent Document 1: JP 2005-62023 A

DISCLOSURE OF THE INVENTION

Problem to be Solved by the Invention

In a case of using a microarray in which a sample is disposed on a surface of a flat substrate such as slide glass, the thickness of the sample is small in an irradiation direction of the excitation light with respect to the sample, and thus the excitation light can be allowed to sufficiently penetrate into the sample by using the device of the related art which is disclosed in Patent Document 1. Accordingly, it is possible to accurately detect the intensity of fluorescence from the sample.

However, in a case of using a microarray in which a sample is filled in a through-hole formed in a flat plate-shaped member (for example, a fiber type DNA chip (Genopal (registered trademark), manufactured by Mitsubishi Rayon Co., Ltd.); JP 4150330 B2 and JP 3654894 B2), since the thickness of the sample in the irradiation direction of the excitation light is large. Therefore, the excitation light does not sufficiently penetrate into the sample with the device of the related art which is disclosed in Patent Document 1, and thus it is difficult to accurately detect the intensity of fluorescence from the sample.

Accordingly, a main object of the invention is to provide a fluorescence detection device and a fluorescence detection method, which are capable of accurately detecting the intensity of fluorescence from a sample, even when using a microarray in which a sample having a certain degree of thickness in a direction of irradiating the sample with excitation light is disposed.

Means for Solving Problem

To accomplish the above-described object, according to a first aspect of the invention, there is provided a fluorescence detection device that detects fluorescence from a translucent sample containing a fluorescent substance. The fluorescence detection device includes an excitation light irradiation unit that irradiates the sample with excitation light, a detection unit that detects fluorescence from the sample, and an irradiation angle adjustment unit that adjusts an irradiation angle of the excitation light with respect to the sample in accordance with dimensions of the sample.

In addition, in the fluorescence detection device according to the first aspect of the invention, the irradiation angle adjustment unit may adjust the irradiation angle of the excitation light in such a manner that an irradiation angle $\theta$ of the excitation light with respect to the sample satisfies the following formula.

$$\theta \leq \tan^{-1}\frac{y}{2 \times t} + 3° \qquad \text{[Mathematical Formula 1]}$$

(Here, t represents a thickness of the sample, and y represents a width of the sample.)

In addition, in the fluorescence detection device according to the first aspect of the invention, in a case where the thickness of the sample is 0.1 mm to 1 mm, the irradiation angle adjustment unit may adjust the irradiation angle of the excitation light in such a manner that the irradiation angle $\theta$ of the excitation light with respect to the sample is in a range of 15° to 60°.

In addition, the fluorescence detection device according to the first aspect of the invention may further include a condensing lens that is disposed on an optical path of fluorescence directed toward the detection unit from the sample, and focuses the fluorescence on the detection unit. The excitation light irradiation unit may be constituted by a plurality of excitation light irradiation units that are disposed at a uniform angular interval on a circumference centering around an optical axis of the condensing lens, or a ring-shaped excitation light irradiation unit that is disposed around the condensing lens.

In addition, the fluorescence detection device according to the first aspect of the invention may further include a focus adjustment unit that adjusts a distance between the condensing lens and the detection unit, and a microarray, in which the sample is disposed, in an optical axis direction of the condensing lens.

In addition, the fluorescence detection device according to the first aspect of the invention may further include a detection position adjustment unit that relatively moves the condensing lens and the detection unit, and a microarray, in which the sample is disposed, in a direction perpendicular to the optical axis of the condensing lens.

In addition, the fluorescence detection device according to the first aspect of the invention may further include a transmission light irradiation unit that irradiates the sample with the transmission light transmitted through the sample. The detection unit may be disposed on an optical path of the transmission light transmitted through the sample, and may detect the transmission light transmitted through the sample.

In addition, the fluorescence detection device according to the first aspect of the invention may further include a diffusion plate that diffuses the transmission light emitted from the transmission light irradiation unit. The diffusion plate may be disposed on the optical path of the transmission light that is directed toward the sample from the transmission light irradiation unit.

In addition, the fluorescence detection device according to the first aspect of the invention may further include a diffusion plate moving unit that takes in and out the diffusion plate on the optical path of the transmission light directed toward the sample from the transmission light irradiation unit.

In addition, according to a second aspect of the invention, there is provided a fluorescence detection method that uses the fluorescence detection device according to the first aspect of the invention. The fluorescence detection method includes a process of irradiating the sample with the excitation light by the extraction light irradiation unit to excite a fluorescent substance contained in the sample, and a process of detecting fluorescence emitted from the fluorescent substance, which is excited, by the detection unit.

In addition, in the fluorescence detection method according to the second aspect of the invention, the fluorescence detection device may include a condensing lens that is disposed on an optical path of fluorescence directed toward the detection unit from the sample, and focuses the fluorescence on the detection unit, and a focus adjustment unit that adjusts a distance between the condensing lens and the detection unit, and a microarray, in which the sample is disposed, in an optical axis direction of the condensing lens. The fluorescence detection method may further include a process of adjusting a distance between the condensing lens and the detection unit, and the microarray in an optical axis direction of the condensing lens by the focus adjustment unit to focus the condensing lens on the sample. The process of irradiating the sample with the excitation light may be performed after the process of focusing condensing lens on the sample.

In addition, in the fluorescence detection method according to the second aspect of the invention, the fluorescence detection device may include a transmission light irradiation unit that irradiates the sample with transmission light that is transmitted through the sample. The process of focusing the condensing lens on the sample may include a process of irradiating the sample with the transmission light by the transmission light irradiation unit, a process of detecting the transmission light transmitted through the sample by the detection unit while changing a distance between the condensing lens and the detection unit, and the microarray in the optical axis direction of the condensing lens step by step by the focus adjustment unit, and a process of determining a position at which the condensing lens is focused on the sample on the basis of an image of the transmission light which is detected by the detection unit.

In addition, in the fluorescence detection method according to the second aspect of the invention, the fluorescence detection device may include a detection position adjustment unit that relatively moves the condensing lens and the detection unit, and the microarray in a direction perpendicular to the optical axis of the condensing lens. The process of detecting fluorescence may include a process of relatively moving the condensing lens and the detection unit, and the microarray in a direction perpendicular to the optical axis of the condensing lens by the detection position adjustment unit, and a process of detecting fluorescence, which is emitted from the fluorescent substance that is excited, for every movement by the detection position adjustment unit.

In addition, in the fluorescence detection method according to the second aspect of the invention, the fluorescence detection device may include a diffusion plate that diffuses the transmission light emitted from the transmission light irradiation unit. The process of irradiating the sample with the transmission light may include a process of disposing the diffusion plate on the optical path of the transmission light that is directed toward the sample from the transmission light irradiation unit. The process of irradiating the sample with the excitation light may include a process of removing the diffusion plate from the optical path of the transmission light that is directed toward the sample from the transmission light irradiation unit.

Effect of Invention

According to the fluorescence detection device and the fluorescence detection method of the invention, it is possible to suppress device background rising due to intrinsic fluorescence of the condensing lens, and it is possible to accurately detect the intensity of fluorescence from a sample even when using a microarray in which a sample having a certain degree of thickness in a direction of irradiating the sample with excitation light is disposed.

MODE(S) FOR CARRYING OUT THE INVENTION (1) Microarray

Figure 1:
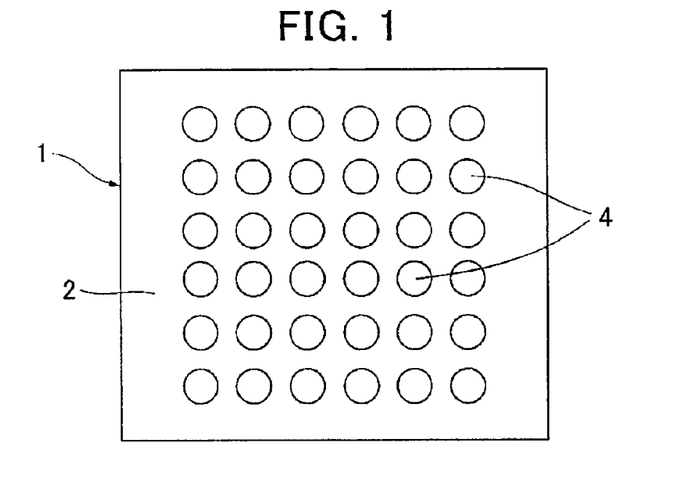
FIG. 1 is a schematic plan view of a microarray that is applied to a fluorescence detection device according to an embodiment of the invention.

First, an example of a microarray that is applied to a fluorescence detection device of an embodiment of the invention will be described with reference to FIG. 1. FIG. 1 is a schematic plan view of the microarray that is applied to the fluorescence detection device of the embodiment of the invention. On the other hand, the microarray that is applied is not limited to the microarray of FIG. 1, and various microarrays in which a sample having a certain degree of thickness is disposed may be applied to the fluorescence detection device of the embodiment of the invention.

For example, the microarray 1 of FIG. 1 includes a flat plate-shaped member 2 that does not transmit light. In the member 2, a plurality of samples 4 are disposed to penetrate through both surfaces of the member 2. The shape of each of the samples 4 is not particularly limited. However, it is preferable that the sample 4 have a circular cross-section. Ecology-related substances, which may be a probe that performs hybridization with a clinical specimen, are fixed to the sample 4. The probe is fixed to the inside of the sample 4 in a direct manner or in an indirect manner through gel. A material of the member 2 is not particularly limited. However, for example, a material, which is obtained by adding carbon black to a resin such as acryl, polycarbonate, and urethane, which is less likely to reflect light, and which is less likely to transmit light, is preferable.

The gel that is used to fix the probe is not particularly limited, but examples thereof may include gel that is obtained by copolymerizing at least one kind of monomers such as acrylamide, N,N-dimethylacrylamide, N-isopropylacrylamide, N-acryloylamino ethoxyethanol, N-acryloyl aminopropanol, N-methylol acrylamide, N-vinylpyrrolidone, hydroxyethyl methacrylate, (meth)acrylic acid, and allyl dextrin, and multifunctional monomers such as methylene bis (meth)acryl amide, and polyethylene glycol di(meth)acrylate. Additionally, examples of the gel, which can be used in the microarray 1, includes gel of agarose, alginate, dextran, polyvinyl alcohol, polyethylene glycol, and the like, gel obtained by crosslinking these substances, and the like.

The microarray 1 can be produced by a method disclosed in JP 2000-270878 A. The fluorescence detection device may measures one sheet of the microarray 1 alone, or may measures a plurality of the microarrays 1, each being disposed in each section of a vessel (so-called well plate) that are divided in a plurality of sections.

(2) Fluorescence Detection Device

Figure 2:
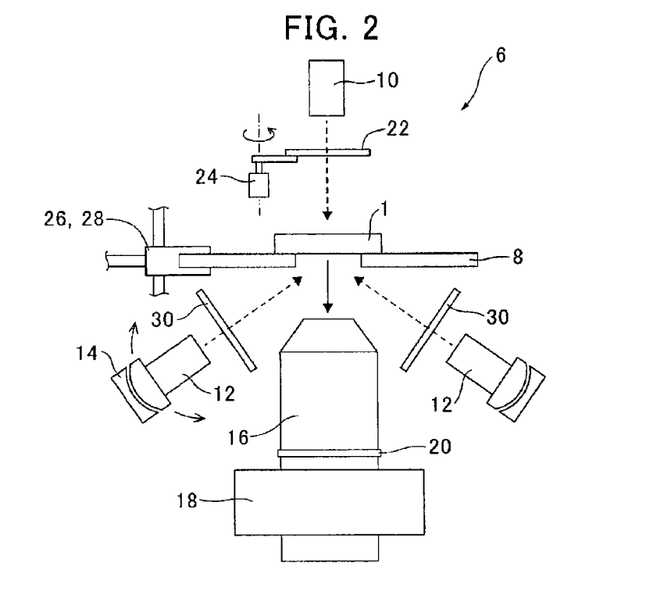
FIG. 2 is a schematic view illustrating a configuration of the fluorescence detection device according to the embodiment of the invention.

Next, a configuration of the fluorescence detection device of a preferred embodiment of the invention will be described with reference to FIGS. 2 and 3. FIG. 2 is a view schematically illustrating a configuration of the fluorescence detection device according to the embodiment of the invention.

As shown in FIG. 2, the fluorescence detection device 6 includes a loading stage 8 on which the microarray 1 is loaded. A transmission light irradiation unit 10, which emits transmission light that is transmitted through the gel in the microarray 1, is provided on an upper side of the loading stage 8. In addition, an excitation light irradiation unit 12 that emits excitation light from an inclined lower side of the microarray 1, and an irradiation angle adjustment unit 14 that adjusts an irradiation angle of the excitation light that is emitted to the sample 4 of the microarray 1 are provided on a lower side of the loading stage 8. In addition, a condensing lens 16, which condenses the transmission light transmitted through the gel inside the microarray 1 and fluorescence from the microarray 1, is provided on a lower side of the loading stage 8. The condensing lens 16 is disposed in such a manner that an optical axis becomes perpendicular to a surface direction of the microarray 1 provided on the loading stage 8. A detection unit 18, which detects the transmission light and the fluorescence that are focused by the condensing lens 16, is provided on a lower side of the condensing lens 16. The detection unit 18 is provided with a fluorescence filter 20 which transmits the fluorescence emitted from the sample 4 inside the microarray 1, and does not transmit excitation light that excites a fluorescent substance in order for excitation light or ambient light not to be incident to the detection unit 18.

The transmission light irradiation unit 10, the loading stage 8, the condensing lens 16, and the detection unit 18 are disposed on an optical axis of the condensing lens 16 in this order. In addition, the excitation light irradiation unit 12 is provided in such a manner that the detection unit 18 does not enter an optical path of the excitation light, that is, the excitation light irradiation unit 12 is provided to irradiate the microarray 1 with the excitation light from a position at which the excitation light is not directly incident to the condensing lens 16 in a direct manner or an indirect manner through a light guide unit such as an optical fiber.

(2-1) Transmission Light Irradiation Unit

The transmission light irradiation unit 10 is disposed on the optical axis of the condensing lens 16 in order to emit the transmission light perpendicularly to the surface of the microarray 1 from an upper side of the microarray 1 that is loaded on the loading stage 8.

A kind of light sources that is used for the transmission light irradiation unit 10 is not particularly limited. However, a light source capable of emitting light of a wavelength with which the light is transmitted through the fluorescence filter 20 is used.

For example, when the sample 4 contains a fluorescent dye Cy5 (emits fluorescence of 660 nm when being irradiated with excitation light of 650 nm), the fluorescence filter 20 configured to transmit only light of 658 nm to 665 nm is used in order for only the fluorescence from the sample 4 to reach the detection unit 18. In this case, a light source that can emit light of a wavelength of 658 nm to 665 nm is used for the transmission light irradiation unit 10.

As the light source that is used for the transmission light irradiation unit 10, for example, a halogen lamp, an LED, laser, and the like may be used. Among these, a surface irradiation type LED, which is capable of irradiating the entire samples 4 of the microarray 1 with transmission light, is preferable.

The intensity of the transmission light that is emitted from the transmission light irradiation unit 10, or a distance from the transmission light irradiation unit 10 to the microarray 1 or the condensing lens 16 is set to allow the transmission light to reach the condensing lens 16.

In addition, according to necessity, a diffusion plate 22 that diffuses the transmission light emitted from the transmission light irradiation unit 10 may be disposed between the transmission light irradiation unit 10 and the microarray 1 to suppress unevenness in a light quantity when the transmission light reaches the microarray 1. For example, the diffusion plate 22 is constituted by a white acrylic plate, a transparent glass plate to which paper is adhered, and the like.

The diffusion plate 22 is supported by a diffusion plate moving unit 24. The diffusion plate moving unit 24 takes in and out the diffusion plate 22 on an optical path of the transmission light that is directed toward the sample 4 from the transmission light irradiation unit 10. The diffusion plate moving unit 24 is constituted by a rotary solenoid or a DC motor. The diffusion plate 22 is connected to a drive shaft of the diffusion plate moving unit 24 through a deceleration mechanism or in a direct manner, and is configured to be movable between a position on the optical path of the transmission light that is directed toward the sample 4 from the transmission light irradiation unit 10 and a position deviated from the optical path of the transmission light that is directed toward the sample 4 from the transmission light irradiation unit 10 in accordance with an operation of the diffusion plate moving unit 24.

(2-2) Loading Stage

The microarray 1 that is an object to be measured is loaded on the loading stage 8. In the loading stage 8, a window for transmission of transmission light, excitation light, fluorescence emitted from the sample 4, and the like is provided, or a hole is formed. The loading stage 8 may load a plurality of the microarrays 1.

The loading stage 8 is supported by a detection position adjustment unit 26 that relatively moves the condensing lens 16 and the detection unit 18, and the microarray 1 in a direction perpendicular to the optical axis of the condensing lens 16. For example, the detection position adjustment unit 26 is constituted by using a biaxial XY stage for microscopes, and the like.

In addition, the loading stage 8 is supported by a focus adjustment unit 28 that adjusts a distance between the condensing lens 16 and the detection unit 18, and the microarray 1 in an optical axis direction of the condensing lens 16. For example, the focus adjustment unit 28 is constituted by using a Z stage for microscopes, and the like, and moves the loading stage 8 along the optical axis of the condensing lens 16.

(2-3) Excitation Light Irradiation Unit

The excitation light irradiation unit 12 emits light of a wavelength component that excites the fluorescent substance in the sample 4 disposed in the microarray 1. For example, as the excitation light irradiation unit 12, an LED, laser, a high-pressure mercury lamp, a xenon lamp, a metal halide lamp, and the like may be used. In addition, light from the light source may be guided by a fiber or lens for irradiation. The excitation light irradiation unit 12 is supported by the irradiation angle adjustment unit 14.

It is preferable that a luminance distribution of light emitted from the excitation light irradiation unit 12 be as uniform as possible and the luminance distribution may be corrected by, for example, a known method such as shading correction. In addition, it is preferable that the intensity of light emitted from the excitation light irradiation unit 12 be as intense as possible.

An excitation filter 30 is disposed between the excitation light irradiation unit 12 and the microarray 1 to limit a wavelength component of the excitation light emitted from the excitation light irradiation unit 12 to a wavelength component that excites the fluorescent substance in the sample 4. The excitation filter 30 transmits only light of a wavelength component that excites the fluorescent substance in the sample 4, and cuts out light of other wavelength components.

For example, in a case of using a fluorescent dye Cy5 (emits fluorescence of 660 nm when being irradiated with excitation light of 650 nm), the excitation filter 30 configured to transmit only light of a wavelength of approximately 650 nm is used in order to irradiate the sample 4 with only the excitation light. According to this, it is possible to prevent the microarray 1 being irradiated with light of a wavelength of 660 nm, and thus it is possible to prevent the light of a wavelength of 660 nm, which is reflected on a surface of the microarray 1, from being incident to the condensing lens 16 and raising a background.

Figure 3:
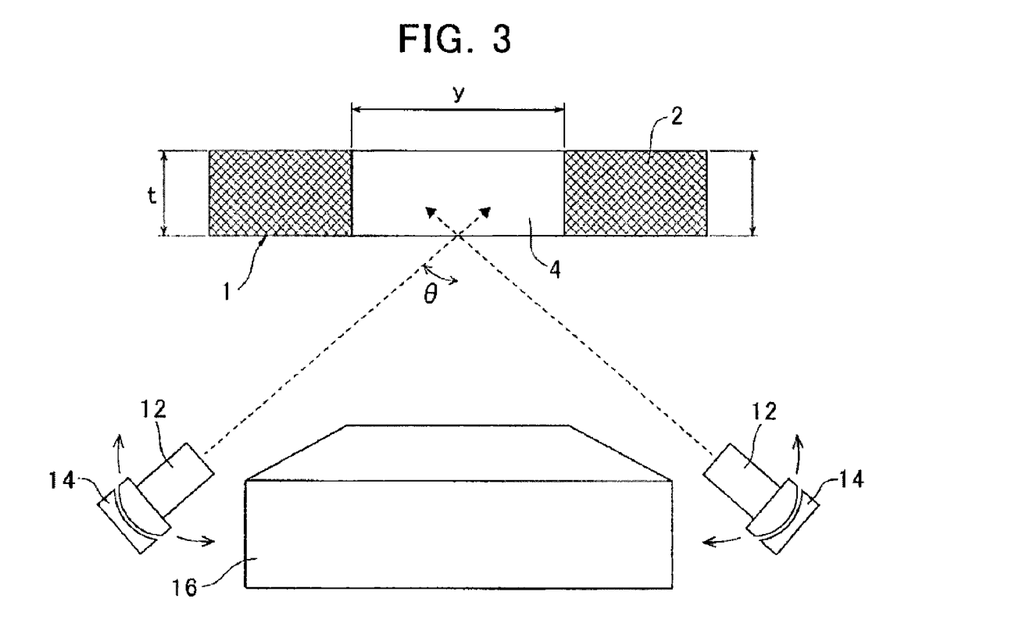
FIG. 3 is an enlarged side view illustrating an irradiation angle of excitation light with respect to a sample in the fluorescence detection device according to the embodiment of the invention.

FIG. 3 is an enlarged side view illustrating an irradiation angle of the excitation light with respect to the sample 4 in the fluorescence detection device 6 according to the embodiment of the invention. Here, the "irradiation angle" represents an irradiation angle (θ in FIG. 3) with respect to a lower surface of the sample 4 of the microarray 1 that is loaded on the loading stage 8. That is, the lower surface of the sample 4 is irradiated with the excitation light from the excitation light irradiation unit 12 at the irradiation angle θ in a state in which a position of the microarray 1 on a horizontal surface of the loading stage 8 is set in order for a central axial line of the sample 4 and the optical axis of the condensing lens 16 to be aligned.

It is preferable that the irradiation angle θ of the excitation light that is incident to the sample 4 from the excitation light irradiation unit 12 be in a range of 15° to 60° with respect to the lower surface of the sample 4. When the irradiation angle θ is set to 15° or more, it is possible to prevent the excitation angle from being cut off by the condensing lens 16, or it is possible to prevent the excitation light irradiation unit 12 and the condensing lens 16 from coming into contact with each other. In addition, when the irradiation angle θ is set to 60° or less, it is possible to allow the excitation light to sufficiently penetrate into the sample 4 having a certain degree of thickness, and thus fluorescence from the sample 4 can be accurately detected. The irradiation angle θ of the excitation light is more preferably in a range of 15° to 55°, and still more preferably in a range of 15° to 45°.

In addition, the irradiation angle θ of the excitation light may be adjusted in such a manner that the irradiation angle θ satisfies the following formula.

[Mathematical Formula 2]

$$\theta \leq \tan^{-1} \frac{y}{2 \times t} + 3° \quad (1)$$

Here, "t" represents the thickness (mm) of the sample 4, and "y" represents the major axis or the diameter (mm) of the sample 4. It is preferable that the thickness t of the sample 4 be in a range of 0.1 mm to 1 mm, more preferably 0.1 mm to 0.5 mm, and still more preferably 0.1 mm t 0.25 mm. The diameter y of the sample 4 may be set in a range capable of realizing a preferred irradiation angle θ.

The irradiation angle θ of the excitation light that is incident to the sample 4 from the excitation light irradiation unit 12 is adjusted by the irradiation angle adjustment unit 14. The irradiation angle adjustment unit 14 rotates and moves the excitation light irradiation unit 12 along an arc centering around the lower surface of the sample 4 irradiated with the excitation light, and is constituted by, for example, a manual or automatic gonio-stage.

The irradiation angle adjustment unit 14 manually or automatically rotates and moves the excitation light irradiation unit 12 to realize the irradiation angle θ that is determined in accordance with the thickness t of the sample 4 as described above.

It is preferable to irradiate the sample 4 with uniform excitation light in which an irradiation distribution is suppressed, and thus it is preferable to provide a plurality (two or more) of the excitation light irradiation unit 12. The number of the excitation light irradiation unit 12 is not particularly limited. However, even in a case of 8 or more, additional improvement in an effect is not obtained, and thus it is preferable to provide 2 to 8 excitation light irradiation units 12.

In a case of using a plurality of the excitation light irradiation units 12, it is preferable to dispose the excitation light irradiation units 12 uniformly on a circumference centering around the optical axis of the condensing lens 16. For example, in a case of disposing four excitation light irradiation units 12, the excitation light irradiation units 12 are disposed on the circumference centering around the optical axis of the condensing lens 16 at an interval of 90°.

In addition, an annular excitation light irradiation unit 12 may be disposed around the condensing lens 16. For example, the annular excitation light irradiation unit 12 is constituted by mounting light sources on a flexible annular substrate in a high density. In this case, the annular excitation light irradiation unit 12 is disposed in such a manner that the central axial line having an annular shape becomes perpendicular to the surface direction of the microarray 1. The irradiation angle adjustment unit 14 changes the inclination of the flexible annular substrate to realize the irradiation angle θ that is determined in accordance with the thickness t of the microarray as described above. It is also possible to suppress the irradiation distribution of the excited light that is incident to the sample 4 by the annular excitation light irradiation unit.

A distance between the excitation light irradiation unit 12 and the microarray 1 may be appropriately selected in accordance with the intensity of the excitation light for irradiation, the number of excitation light irradiation units 12, and the like. The shorter the distance between the excitation light irradiation unit 12 and the microarray 1 is, the less attenuation of the excitation light occurs. Accordingly, it is preferable that the excitation light irradiation unit 12 be close to the microarray 1. However, when the distance between the excitation light irradiation unit 12 and the microarray 1 is too short, the excitation light irradiation unit 12 enters a visual field of the condensing lens 16, and thus it is preferable to retain a distance to a certain degree at which the excitation light irradiation unit 12 does not enter the visual field of the condensing lens 16.

(2-4) Condensing Lens

As the condensing lens 16, an objective lens for microscopes, and the like may be used. The microarray detection unit 18 is used for detection of the fluorescent emitted from the sample 4, and thus it is preferable to use a lens, which is designed for fluorescence microscopes and in which intrinsic fluorescence is less, for the condensing lens 16.

A kind of the condensing lens 16 is not particularly limited. However, it is preferable to use a lens in which an operating length (a distance between the microarray 1 and the front end of the condensing lens 16 when being focused on the microarray 1) is long and an outer diameter is small to prevent the excitation light, which is emitted from the excitation light irradiation unit 12, from being shielded by the condensing lens 16.

(2-5) Detection Unit

As the detection unit 18, a CCD sensor, a CMOS sensor, a line sensor, and the like may be used. Particularly, as the detection unit 18, it is preferable to use a cooling CCD camera equipped with a sensor cooling function to detect or image weak fluorescence, which is emitted from the sample 4 of the microarray 1, with small noise. The detection unit 18 is embedded in the fluorescence detection device 6 together with a lens barrel (not shown in the drawing) in such a manner that the optical axis of the detection unit 18 is aligned with the optical axis of the condensing lens 16 (is linearly disposed on the optical axis).

In addition, the fluorescence filter 20, which is configured to transmit fluorescence emitted from the sample 4 of the microarray 1 and not to transmit excitation light that excites a fluorescent substance, may be disposed in the detection unit 18. For example, in a case of using a fluorescent dye Cy5 (emits fluorescence of 660 nm when being irradiated with excitation light of 650 nm), a filter, which is configured to transmits only light of, for example, 658 nm to 665 nm in order for reflected excitation light, light incident from the outside of the sample 4, and the like not to enter the detection unit 18, is used as the fluorescence filter 20. In this manner, when using the fluorescence filter 20, only the fluorescence is allowed to reach the detection unit 18.

The fluorescence (imaged image) that is detected by the detection unit 18 is transmitted to operational equipment such as PC, and image analysis and data processing are performed according to an arbitrary algorithm. A grayscale value for each of the samples 4 of the microarray 1 is digitized during the data processing and is output as CSV data.

(3) Method of Detecting Microarray (3-1) Process of Adjusting Focus Using Transmission Light Image of Microarray which is Obtained by Irradiating Microarray with Transmission Light The microarray 1 is set on the loading stage 8, and the loading stage 8 is moved along the optical axis of the condensing lens 16 by the focus adjustment unit 28 in such a manner that a distance between the front end of the condensing lens 16 and the microarray 1 becomes the operating distance (already known according to specifications of the condensing lens 16). Then, the diffusion plate 22 is disposed by the diffusion plate moving unit 24 on the optical path of the transmission light directed toward the sample 4 from the transmission light irradiation unit 10. Next, in a state in which the microarray 1 is irradiated with the transmission light through the diffusion plate 22 by the transmission light irradiation unit 10, a transmission image of the microarray 1, which is formed by the transmission light transmitted through the sample 4 of the microarray 1, is imaged by the detection unit 18 while moving the loading stage 8 back and forth, for example, in a distance of 1 mm by a pitch of 0.05 mm along the optical axis of the condensing lens 16. In addition, a position of the loading stage 8 at which a transmission image having the highest contrast (the maximum contrast) is imaged is determined as a focal position at which the condensing lens 16 is focused on the sample 4. Transmission light (transmission image) that is detected at the focal position is transmitted to the operation equipment, and is used for digitization processing in a process to be described later in (3-4).

(3-2) Process of Irradiating Sample of Microarray with Excitation Light to Excite Fluorescent Substance Coupled to Sample Subsequently, the transmission light irradiation by the transmission light irradiation unit 10 is stopped, and the diffusion plate 22 is removed from the optical path of the transmission light that is directed toward the sample 4 from the transmission light irradiation unit 10 by the diffusion plate moving unit 24. Next, the sample 4 of the microarray 1 is irradiated with the excitation light by the excitation light irradiation unit 12. Conditions such as the irradiation angle of the excitation light are the same as described above. When the sample 4 is irradiated with the excitation light, the fluorescent substance coupled to the sample 4 can be excited.

(3-3) Process of Detecting Fluorescence from Excited Sample

In a state in which the sample 4 of the microarray 1 is irradiated with the excitation light by the excitation light irradiation unit 12, fluorescence from the sample 4 of the microarray 1 is detected (fluorescence image is imaged) by the detection unit 18. Here, the detected fluorescence (imaged fluorescence image) is transmitted to the operation equipment, and is provided to digitization processing in a process to be described later in (3-4).

(3-4) Process of Performing Digitization Processing

In the process described in (3-1), the transmission light is transmitted through a portion of the sample 4 of the microarray 1, and is not transmitted through the other portions including the non-translucent member 2. Accordingly, when the transmission image obtained in the process of (3-1) is digitized on the basis of a threshold value that is arbitrarily set, the portion of the sample 4 is expressed by "1", and the other portions including the non-translucent member 2 is expressed by "0". Central coordinates of the respective samples 4 are calculated from the image that is digitized, and the central coordinates that are calculated are stored.

Then, in the fluorescence image obtained in the process described in (3-3), a grayscale value (numerical value indicating brightness of light detected by the detection unit 18) of a pixel in a region surrounded by a circle having a predetermined radius (inner diameter of the samples 4 of the microarray 1) with the central coordinates of each of samples 4 set as the center is measured. According to this, an amount of fluorescence of the sample 4 of the microarray 1 is detected.

(3-5) Process of Moving Loading Stage

In a case where a plurality of microarrays 1 are loaded on the loading stage 8, the loading stage 8 is moved by the detection position adjustment unit 26 to detect fluorescence emitted from the samples 4 of each of the microarrays 1. That is, according to the above-described processes, fluorescence emitted from the sample 4 of one microarray 1 is detected. Then, the loading stage 8 is moved in a direction perpendicular to the optical axis of the condensing lens 16 by the detection position adjustment unit 26, and the microarray 1 for which detection of fluorescence is not performed is disposed on the optical axis of the condensing lens 16. In addition, fluorescence emitted from the sample 4 of the microarray 1 is detected according to the above-described respective processes. The movement of the loading stage 8 and the detection of fluorescence emitted from the sample 4 of the microarray are repeated with respect to all of the microarrays 1 that are loaded on the loading stage 8.

EXAMPLES

Hereinafter, examples of the invention will be described.

1. Production of Microarray

First, two porous sheets having a thickness of 0.1 mm were prepared. A total of 25 through-holes having a diameter of 0.32 mm are arranged at the central portion of the porous plate in a lattice shape of 5 rows×5 columns at an interval of 0.42 mm. A polycarbonate hollow fiber (an outer diameter: 0.28 mm, an inner diameter: 0.18 mm, and a length: 500 mm) colored with carbon black was allowed to penetrate through all of the through-holes of the porous plates. The two porous plates through which the hollow fiber penetrate were spaced away from each other by 50 mm, and a polyurethane resin colored with carbon black was filled between the porous plates spaced away from each other, thereby obtaining a prismatic hollow-fiber arrangement body which has a portion not fixed with the resin at both ends and has dimensions of a width of 20 mm, a height of 20 mm, and a length of 50 mm.

A solution, which was obtained by mixing dimethylacrylamide (3.8% by mass) gel precursor solution, and a Cy5 fluorescent substance that was diluted and adjusted in a concentration ratio shown in Table 1, was filled in each of the hollow fibers in the hollow-fiber arrangement body that was obtained, and the gel precursor solution and the Cy5 fluorescent substance were subjected to polymerization. Then, a thin piece having a thickness of 0.25 mm was cut out from the prismatic hollow-fiber arrangement body along a direction perpendicular to the axial direction of the hollow fiber by a microtome, thereby obtaining a microarray (capillary array sheet). The microarray that was obtained was placed on slide glass, was covered with cover glass in a state of being immersed in water, and was set on the loading stage.

TABLE 1

| No. | Cy5 concentration ratio |
| --- | --- |
| 1 | 1 |
| 2 | 0.2 |
| 3 | 0.04 |
| 4 | 0.008 |
| 5 | 0.0016 |
| 6 | 0.00032 |

2. Configuration of Fluorescence Detection Device

The fluorescence detection device shown in FIG. 1 was constituted by components shown in Table 2.

TABLE 2

| Constituent Component | Details | Dealer | Mode and the like |
| --- | --- | --- | --- |
| Excitation light irradiation unit | Red LED | CCS Co., Ltd. | HLV2 series RED |
| Transmission light irradiation unit | White LED | CCS Co., Ltd. | HPR series |
| Fluorescence filter | Fluorescence filter for Cy5 | Omega Optical Co., Ltd. | XF3030 |
| Excitation filter | Excitation filter for Cy5 | Omega Optical Co., Ltd. | XF1026 |
| Condensing lens | Objective lens | Olympus Co., Ltd. | XLFLUOR 2X |
| Diffusion plate | White acrylic plate | — | White 3 mm |
| Detection unit | Cooling CCD camera | BITRAN CORPORATION | BS-41L |

Example 1

In the microarray that was used in Example 1, as described above, the thickness of a sample was 0.25 mm, and the diameter of the sample was 0.18 mm. In this case, according to Formula (1) described above, the irradiation angle θ was calculated as approximately 20°. Accordingly, the excitation light irradiation unit was disposed in such a manner that the surface of the sample of the microarray was irradiated with the excitation light at an irradiation angle of 20°. Four excitation light irradiation units were uniformly disposed at an interval of 90° on a circumference centering around the optical axis of the condensing lens. When setting a distance between the condensing lens and the microarray to 21 mm, a light quantity distribution in an imaging range of the condensing lens was set in such a manner that a difference in a light quantity between the center and the periphery became approximately 5%.

First, in a state in which the sample of the microarray was irradiated with only the transmission light by the transmission light irradiation unit, a transmission image, which was formed by the transmission light transmitted through the sample of the microarray, was imaged by the detection unit while moving the loading stage back and forth, for example, in a distance of 1 mm by a pitch of 0.05 mm along the optical axis of the condensing lens. In addition, a position of the loading stage at which a transmission image having the highest contrast (the maximum contrast) was imaged was determined as a focal position. In addition, the transmission image that was imaged at this focal position was digitized on the basis of a predetermined threshold value, and central coordinates of each sample were calculated.

Figure 4:
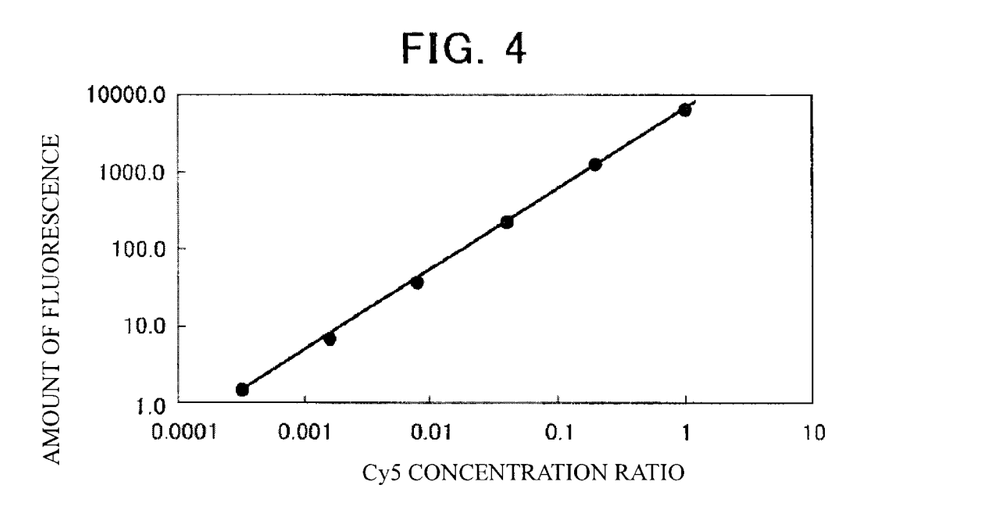
FIG. 4 is a diagram illustrating detection results of an amount of fluorescence of the sample of the microarray by a fluorescence detection device of Example 1 of the invention in which the irradiation angle of the excitation light with respect to the sample is set to 20°.

FIG. 4 is a diagram illustrating detection results of an amount of fluorescence of the sample of the microarray by the fluorescence detection device of Example 1 of the invention in which the irradiation angle of the excitation light with respect to the sample of the microarray was set to 20°. In FIG. 4, the horizontal axis represents a concentration ratio of the Cy5 fluorescent substance, and the vertical axis represents an amount of fluorescence which is detected by the fluorescence detection device. From detection results of fluorescence from the sample of the microarray by the fluorescence detection device of Example 1, as shown in FIG. 4, high linearity was obtained between the concentration ratio of Cy5 and the amount of fluorescence which was detected over the entire range of the Cy5 concentration ratio from 0.00032 to 1. That is, it could be seen that fluorescence from the sample was very accurately detected by the fluorescence detection device of Example 1.

Example 2

Figure 5:
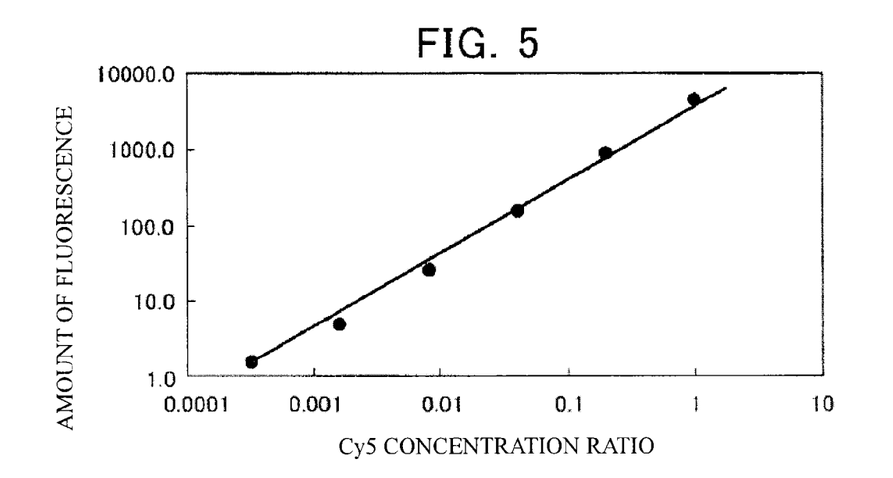
FIG. 5 is a diagram illustrating detection results of an amount of fluorescence of the sample of the microarray by a fluorescence detection device of Example 2 of the invention in which the irradiation angle of the excitation light with respect to the sample is set to 55°.

FIG. 5 is a diagram illustrating detection results of the amount of fluorescence of the sample of the microarray by a fluorescence detection device of Example 2 of the invention in which the irradiation angle of the excitation light with respect to the sample of the microarray was set to 55°. Experiment was performed in the same manner as Example 1 except that the irradiation angle of the excitation light with respect to the sample of the microarray was set to 55°. In Example 2, as shown in FIG. 5, high linearity was obtained between the concentration ratio of Cy5 and the amount of fluorescence which was detected over the entire range of the Cy5 concentration from 0.00032 to 1. That is, it could be seen that fluorescence from the sample was very accurately detected by the fluorescence detection device of Example 2.

Comparative Example 1

Figure 6:
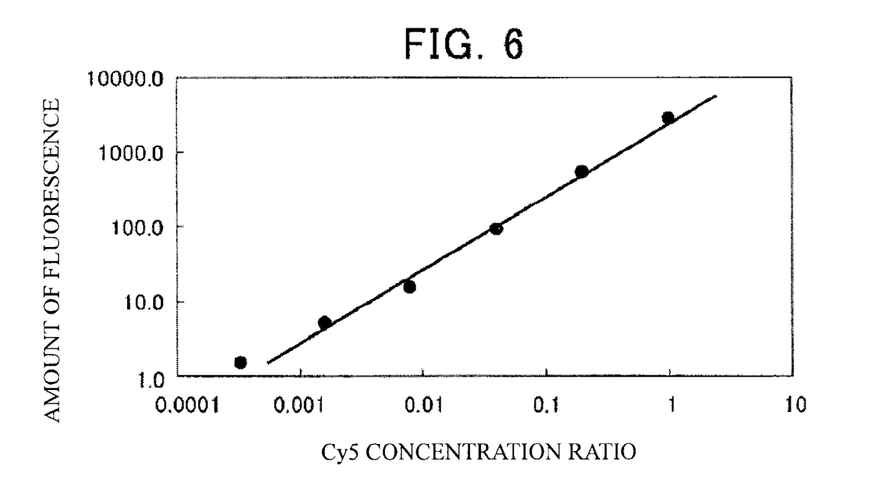
FIG. 6 is a diagram illustrating detection results of an amount of fluorescence of the sample of the microarray by a fluorescence detection device of Comparative Example 1 of the invention in which the irradiation angle of the excitation light with respect to the sample is set to 70°.

FIG. 6 is a diagram illustrating detection results of the amount of fluorescence of the sample of the microarray by a fluorescence detection device of Comparative Example 1 of the invention in which the irradiation angle of the excitation light with respect to the sample of the microarray is set to 70°. Experiment was performed in the same manner as Example 1 except that the irradiation angle of the excitation light with respect to the sample of the microarray was set to 70°. In Comparative Example 2, as shown in FIG. 6, linearity was obtained between the concentration ratio of Cy5 and the amount of fluorescence which was detected in a range of the Cy5 concentration of 0.0016 to 1, but linearity was not obtained between the concentration ratio of Cy5 and the detected amount of fluorescence in a range of the Cy5 concentration of 0.0016 or less. That is, in the fluorescence detection device of Comparative Example 1, fluorescence from the sample was not detected accurately.

Comparative Example 2

Figure 7:
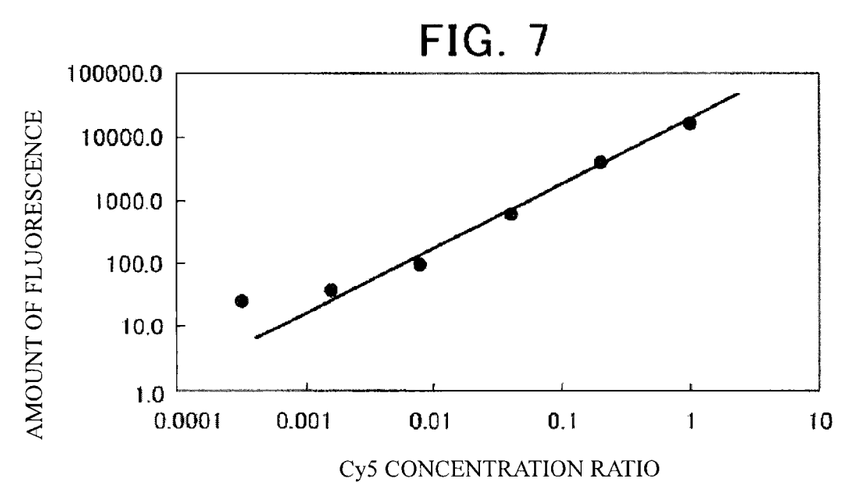
FIG. 7 is a diagram illustrating detection results of an amount of fluorescence of the sample of the microarray by a typical coaxial vertical type fluorescence microscope, which uses a high-pressure mercury lamp as an excitation light source, of Comparative Example 2.

FIG. 7 is a diagram illustrating detection results of an amount of fluorescence of the sample of the microarray by a typical coaxial vertical type fluorescence microscope (ECLIPSE E600, manufactured by Nikon Corporation), which uses a high-pressure mercury lamp as an excitation light source, of Comparative Example 2. In Comparative Example 2, a device background was high due to intrinsic fluorescence inside the condensing lens, and thus as shown in FIG. 7, linearity was obtained between the concentration ratio of Cy5 and the amount of fluorescence which was detected in a range of the Cy5 concentration of 0.0016 to 1, but linearity was not obtained between the concentration ratio of Cy5 and the detected amount of fluorescence in a range of the Cy5 concentration of 0.0016 or less. That is, in the fluorescence microscope of Comparative Example 2, fluorescence from the sample was not detected accurately.

EXPLANATIONS OF LETTERS OR NUMERALS

1: Microarray
2: Non-translucent member
4: Sample
6: Fluorescence detection device
8: Loading stage
10: Transmission light irradiation unit
12: Excitation light irradiation unit
14: Irradiation angle adjustment unit
16: Condensing lens
18: Detection unit
20: Fluorescence filter
22: Diffusion plate
24: Diffusion plate moving unit
26: Detection position adjustment unit
28: Focus adjustment unit
30: Excitation filter

The invention claimed is:

1. A fluorescence detection device, said device comprising:
an excitation light irradiation unit that irradiates a sample with excitation light,
a detection unit that detects fluorescence from the sample, and
an irradiation angle adjustment unit that adjusts an irradiation angle of the excitation light with respect to the sample in accordance with dimensions of the sample,
wherein the irradiation angle adjustment unit adjusts the irradiation angle of the excitation light in such a manner that an irradiation angle θ of the excitation light with respect to a sample satisfies the following formula:

$$\theta \leq \tan^{-1}\frac{y}{2 \times t} + 3°, \qquad \text{formula 1}$$

where t represents a thickness of the sample, and y represents a width of the sample.

2. The fluorescence detection device according to claim 1, further comprising:

a transmission light irradiation unit that irradiates the sample with the transmission light transmitted through the sample, wherein the detection unit is disposed on an optical path of the transmission light transmitted through the sample, and detects the transmission light transmitted through the sample.

3. The fluorescence detection device according to claim 2, further comprising:

a diffusion plate that diffuses the transmission light emitted from the transmission light irradiation unit, wherein the diffusion plate is disposed on the optical path of the transmission light that is directed toward the sample from the transmission light irradiation unit.

4. The fluorescence detection device according to claim 3, further comprising:

a diffusion plate moving unit that takes in and out the diffusion plate on the optical path of the transmission light directed toward the sample from the transmission light irradiation unit.

5. The fluorescence detection device of claim 1 wherein said device is capable of detecting fluorescence from a translucent sample containing a fluorescent substance.

6. A fluorescence detection device, said device comprising:

an excitation light irradiation unit that irradiates a sample with excitation light, a detection unit that detects fluorescence from the sample, and an irradiation angle adjustment unit that adjusts an irradiation angle of the excitation light with respect to the sample in accordance with dimensions of the sample, wherein when the thickness of the sample is from 0.1 mm to 1 mm, the irradiation angle adjustment unit adjusts the irradiation angle of the excitation light such a that the irradiation angle θ of the excitation light with respect to the sample is in a range of 15° to 60°.

7. A fluorescence detection device, said device comprising:

an excitation light irradiation unit that irradiates a sample with excitation light, a detection unit that detects fluorescence from the sample, and an irradiation angle adjustment unit that adjusts an irradiation angle of the excitation light with respect to the sample in accordance with dimensions of the sample, the fluorescence detection device further comprising:

a condensing lens that is disposed on an optical path of fluorescence directed toward the detection unit from the sample, and focuses the fluorescence on the detection unit, and wherein the excitation light irradiation unit is constituted by a plurality of excitation light irradiation units that are disposed at a uniform angular interval on a circumference centering around an optical axis of the condensing lens, or an annular excitation light irradiation unit that is disposed around the condensing lens.

8. The fluorescence detection device according to claim 7, further comprising:

a focus adjustment unit that adjusts a distance between the condensing lens and the detection unit, and a microarray, in which the sample is disposed, in an optical axis direction of the condensing lens.

9. The fluorescence detection device according to claim 7, further comprising:

a detection position adjustment unit that moves the condensing lens, the detection unit, and a microarray, in which the sample is disposed, in a direction perpendicular to the optical axis of the condensing lens.

10. A fluorescence detection method comprising:

irradiating a sample with excitation light from an extraction light irradiation unit to excite a fluorescent substance contained in the sample;

detecting fluorescence emitted from the fluorescent substance by a detection unit;

adjusting a distance between a condensing lens, the detection unit and a microarray in an optical axis direction of the condensing lens by a focus adjustment unit to focus the condensing lens on the sample; and irradiating the sample with the excitation light after focusing the condensing lens on the sample.

11. The fluorescence detection method according to claim 10, wherein focusing the condensing lens on the sample comprises:

irradiating the sample with light that is transmitted through the sample by a transmission light irradiation unit, detecting the transmission light transmitted through the sample by the detection unit while changing a distance between the condensing lens and the detection unit, and the microarray in the optical axis direction of the condensing lens incrementally by the focus adjustment unit, and determining a position at which the condensing lens is focused on the sample on the basis of an image of the transmission light which is detected by the detection unit.

12. The fluorescence detection method according to claim 11, wherein the process of detecting fluorescence comprises:

moving the condensing lens and the detection unit, and the microarray in a direction perpendicular to the optical axis of the condensing lens by the detection position adjustment unit, and detecting fluorescence emitted from the fluorescent substance that is excited, for every movement by the detection position adjustment unit.

13. The fluorescence detection method according to claim 11, wherein irradiating the sample with the transmission light comprises disposing a diffusion plate that diffuses the transmission light emitted from the transmission light irradiation unit on the optical path of the transmission light that is directed toward the sample from the transmission light irradiation unit, and irradiating the sample with the excitation light which comprises removing the diffusion plate from the optical path of the transmission light that is directed toward the sample from the transmission light irradiation unit.

* * * * *